(12) United States Patent
Wieselblad

(10) Patent No.: US 9,095,658 B2
(45) Date of Patent: Aug. 4, 2015

(54) MEDICAMENT DELIVERY DEVICE

(71) Applicant: Anders Wieselblad, Stockholm (SE)

(72) Inventor: Anders Wieselblad, Stockholm (SE)

(73) Assignee: SHL Group AB, Nacka Strand (SE)

( * ) Notice: Subject to any disclaimer, the term of this patent is extended or adjusted under 35 U.S.C. 154(b) by 0 days.

(21) Appl. No.: 14/352,275

(22) PCT Filed: Oct. 4, 2012

(86) PCT No.: PCT/SE2012/051057
§ 371 (c)(1),
(2) Date: Apr. 16, 2014

(87) PCT Pub. No.: WO2013/058698
PCT Pub. Date: Apr. 25, 2013

(65) Prior Publication Data
US 2014/0249482 A1     Sep. 4, 2014

Related U.S. Application Data

(60) Provisional application No. 61/547,917, filed on Oct. 17, 2011.

(30) Foreign Application Priority Data

Oct. 17, 2011     (SE) .................................... 1150961-9

(51) Int. Cl.
*A61M 5/00* (2006.01)
*A61M 5/315* (2006.01)
*A61M 5/24* (2006.01)

(52) U.S. Cl.
CPC ......... *A61M 5/31535* (2013.01); *A61M 5/3155* (2013.01); *A61M 5/31551* (2013.01); *A61M 5/31585* (2013.01); *A61M 5/3157* (2013.01); *A61M 5/31593* (2013.01); *A61M 2005/2407* (2013.01); *A61M 2005/2488* (2013.01); *A61M2005/2492* (2013.01); *A61M 2205/581* (2013.01); *A61M 2205/582* (2013.01)

(58) Field of Classification Search
CPC ..................... A61M 5/31533; A61M 5/31535; A61M 5/31536; A61M 5/31526; A61M 2005/2407; A61M 2005/2488; A61M 5/31551; A61M 5/31585; A61M 2005/2492; A61M 5/31593
USPC ......... 604/211, 207, 208, 209, 187, 198, 194, 604/193, 192, 218, 223, 224, 227, 232
See application file for complete search history.

(56) References Cited

U.S. PATENT DOCUMENTS 5,320,609 A * 6/1994 Haber et al. ................... 604/135
5,674,204 A * 10/1997 Chanoch ....................... 604/211

FOREIGN PATENT DOCUMENTS

| DE | 102009043803 A1 | 4/2011 |
|---|---|---|
| EP | 1541185 A1 | 6/2005 |
| EP | 1601395 B1 | 7/2010 |
| WO | 2004078226 A2 | 9/2004 |
| WO | 2009062686 A1 | 5/2009 |

* cited by examiner

*Primary Examiner* — Bhisma Mehta
*Assistant Examiner* — Hamza Darb
(74) *Attorney, Agent, or Firm* — McDonnell Boehnen Hulbert & Berghoff LLP

(57) ABSTRACT

A medicament delivery device includes a body having a proximal end and a distal end, in turn comprising a distal housing part, and a medicament container holder, adapted to receive a medicament container; a dose setting drum for setting a dose when rotated in a first direction and for delivering a dose when rotated in a second direction, and a drive drum sleeve selectively operably connectable to a piston plunger for delivering a dose.

28 Claims, 13 Drawing Sheets

MEDICAMENT DELIVERY DEVICE

CROSS REFERENCE TO RELATED APPLICATIONS

The present application is a U.S. National Phase Application pursuant to 35 U.S.C. §371 of International Application No. PCT/SE2012/051057 filed Oct. 4, 2012, which claims priority to U.S. Patent Application No. 61/547,917 filed Oct. 17, 2011 and Swedish Patent Application No. 1150961-9 filed Oct. 17, 2011. The entire disclosure contents of these applications are herewith incorporated by reference into the present application.

FIELD OF INVENTION

The present invention relates to a medicament delivery device and in particular a device capable of delivering a dose of medicament set by user before delivery.

BACKGROUND

There are numerous devices for delivering medicament on the market and also patented where the medicament is arranged in a container, such as a syringe, cartridge and the like, and wherein the medicament is exposed to pressure when it is to be delivered. A very common design is a generally tubular compartment having a stopper in one end of the compartment and a delivery member attached to the opposite end of the compartment, such as, e.g., a needle, a nozzle or the like member capable of delivering medicament to a patient.

In order to deliver a quantity of medicament, the stopper is exposed to pressure, i.e. pushed into the compartment by a plunger rod, which could be done manually by a finger, which is the case for simple handheld syringes, or by pressure means such as springs, which is common in automatic or semi-automatic injectors. In this context, the so called pen-injectors are becoming quite common, where the injection is performed by manually pushing at a distal end of the device. With this type of injector there has also been a development regarding delivering different dose quantities with the same device, i.e. to be able to set a certain prescribed dose before delivery.

A number of such devices have been developed, such as the device disclosed in EP-A-1 601 395. Here the device is arranged with a dose setting drum that can be rotated in relation to a housing and a drive sleeve that, upon manual operation by a user, drives a plunger rod to deliver a set dose of medicament. In order to provide the function of setting a dose with the dose setting drum and delivering a dose with the drive sleeve, there has to be some sort of connection/disconnection mechanism between them. Thereby a clutch or unidirectional connection mechanism has been developed for providing the desired function. This solution entails a number of components that are to interact with each other as well as a number of threaded engagement and connection mechanisms that require careful design in order for the manually applied force by a user not to be too large, or the device otherwise will not function properly. There is also a question whether the solution according to EP-A-1 601 395 can provide the possibility of resetting a set dose in a simple and efficient manner.

SUMMARY

An object of the present invention is to provide a medicament delivery device wherein the drawbacks of the state of the art devices are remedied.

In order to overcome one or several of the above-mentioned problems, a medicament delivery device according to independent claim 1 is provided.

Further aspects, improvements and variations are disclosed in the dependent claims, the figures and the description.

In the present application, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site. Further, the term "longitudinal", with or without "axis", refers to a direction or an axis through the device or components thereof in the direction of the longest extension of the device or the component. In a similar manner, the term "transverse", with or without "axis", refers to a direction or an axis through the device or components thereof in a direction generally perpendicular to the longitudinal direction. Also, if nothing else is stated, in the following description wherein the mechanical structure of the device and the mechanical interconnection of its components is described, the device is in an initial non-activated or non-operated state.

The invention provides a medicament delivery device having a housing with a proximal end and a distal end. A hollow piston plunger is arranged within the housing. The piston plunger has a longitudinal axis generally corresponding with the longitudinal direction of the medicament delivery device.

Furthermore, a telescopic dose drum is concentrically arranged between the housing and the piston plunger. The telescopic dose drum is bidirectional movable in relation to the housing and in relation to the piston plunger when setting a dose and delivering a dose.

The medicament delivery device also comprises a piston plunger driving means for driving the hollow piston plunger towards the proximal end. The piston plunger driving means comprises a hollow drive drum sleeve that is movably arranged within the hollow piston plunger and is fixedly connected to the telescopic dose drum. The hollow drive drum sleeve and the hollow piston plunger are releasably coupleable to each other. The piston plunger driving means further comprises a resilient spinning element having a longitudinal rod being movably arranged within the hollow drive drum sleeve. The longitudinal rod and the hollow drive drum sleeve are releasably coupleable to each other; such that after a dose is set, axial movement of the resilient spinning element towards the proximal end forces the longitudinal rod and the hollow drive drum sleeve to couple together and thereby the hollow drive drum sleeve and the hollow piston plunger also to couple together whereby the hollow piston plunger and the telescopic dose drum are displaced towards the proximal end for delivering the set dose, and such that after a set dose is delivered, axial movement of the resilient spinning element towards the distal end forces the longitudinal rod and the hollow drive drum sleeve to decouple and thereby the hollow drive drum sleeve and the hollow piston plunger also to decouple for setting a new dose.

The resilient spinning element may be configured to be axially spaced from a distal part of the hollow drive drum sleeve during setting a dose by a user, and to abut against the distal part of the hollow drive drum sleeve during delivery of a set dose.

The telescopic dose drum preferably comprises a first part (distal part) and a second part (proximal part) that are slidably arranged relative to each other.

The medicament delivery device may further comprise at its distal end a dose setting knob. The dose setting knob may be configured to be grasped by a user for setting a dose when being rotated in a first direction.

According to one embodiment of the medicament delivery device, the dose setting knob is a separate component connected, preferably fixedly connected, with the first part of the dose drum at its distal end. According to another embodiment, the dose setting knob is integral with the first part of the telescopic dose drum. The first part of the telescopic dose drum may be configured to rotationally move distally in the first direction relative to the housing during dose setting by the dose setting knob.

According to an alternative embodiment, the dose setting knob is a separate component connected, preferably fixedly connected, with the drive drum sleeve at its distal end. Alternatively, the dose setting knob is integral with the drive drum sleeve. The drive drum sleeve may be is configured to rotationally move distally in the first direction relative to the housing during dose setting by the dose setting knob.

The medicament delivery device may further comprise a medicament container holder adapted to receive a medicament container.

It is preferred that part of the outer circumferential surface of the piston plunger is threaded. For example, a proximal part of the piston plunger may comprise a threaded structure However, the invention also encompasses that the entire surface of the piston plunger is threaded. On its outer surface, the piston plunger may comprise at least one longitudinal groove, e.g., two grooves. Furthermore, the proximal end of the piston plunger may be arranged with a washer and a stopper. The stopper at the proximal end of the piston plunger may be intended to be movably received inside the medicament container.

The medicament delivery device may further comprise an unidirectional means for preventing movement of the piston plunger in the distal direction during setting a dose.

According to a first preferred embodiment, the unidirectional means comprises an insert having a central longitudinal passage having a first diameter. The passage is provided with threads mating with the threads of the outer circumferential surface of the piston plunger, wherein the insert, in the initial position of the medicament delivery device, is located at the proximal end of the piston plunger. The insert may further comprise at its distal side a central bore coaxial with the central longitudinal passage. The central bore may have a second diameter being larger than the first diameter. Furthermore, the inner surface of the bore may be provided with a circumferentially extending ratchet. The insert may be a separate component being fixedly connected to the housing or may be a component integral with the housing.

The unidirectional means of this embodiment may further comprise a back rotation blocking element that comprises at its circumferential surface at least one arm extending in circumferential direction and being flexible in radial direction. The one or more arms may comprise a ledge having a shape complementary to the ratchet of the insert. The at least one arm with its ledge may be resilient such that rotation of the back rotation blocking element against the ratchet during medicament delivery generates an audible feedback.

The back rotation blocking element may comprise a longitudinal central passage having at least one radially inwardly directed protrusion. The at least one protrusion may be each received in a corresponding longitudinal groove on the outer surface of the piston plunger. This structure provides a rotational lock of the piston plunger but allows a movement of the piston plunger in the longitudinal direction.

According to another embodiment, the unidirectional means comprises an insert having a central longitudinal passage having a first diameter, central longitudinal passage having at least one radially inwardly directed protrusion, the at least one protrusion being each received in a corresponding longitudinal groove on the outer surface of the piston plunger. This structure provides a rotational lock of the piston plunger but allows a movement of the piston plunger in the longitudinal direction. The insert may further comprise at its distal side a central bore coaxial with the central longitudinal passage. The central bore may have a second diameter being larger than the first diameter, the inner surface of the bore being provided with a circumferentially extending ratchet.

In this embodiment, the unidirectional means further comprises a back rotation blocking element having a central longitudinal passage having a first diameter, the passage being provided with threads mating with the threads of the outer circumferential surface of the piston plunger. The back rotation blocking element, in the initial position of the medicament delivery device, may be located at the proximal end of the piston plunger. The back rotation blocking element may comprise at its circumferential surface at least one arm extending in circumferential direction and being flexible in radial direction, the at least one arm comprising a ledge having a shape complementary to the ratchet of the insert.

The ratchet may comprise steep front edges and ramp shaped trailing edges such that the interaction of the ratchet with the at least one arm is to have a unidirectional coupling for the piston plunger.

According to a still further embodiment, the unidirectional means comprises a self-locking thread connection between the threaded mating between the insert and the piston plunger.

The inner circumferential surface of the piston plunger may comprise a plurality of longitudinally extending splines and the drive drum sleeve comprises at least one flexible arm being configured to releasably engage with the plurality of longitudinally extending splines of the piston plunger. It is preferred that the longitudinal rod of the resilient spinning element is operably connected with the hollow drive drum sleeve such that the axial movement of the resilient spinning button in proximal direction forces the at least one flexible arm to engage with the plurality of longitudinally extending splines of the piston plunger.

In the medicament delivery device of a preferred embodiment, the resilient spinning element is configured to stay rotationally immobilized during axial movement thereof.

The outer circumferential surface of the first part of the telescopic dose drum may be threadedly connected to a mating structure on the inner circumferential surface of the housing. The inner circumferential surface of the second part of the telescopic dose drum may be threadedly connected to the threaded outer circumferential surface of the piston plunger. The threaded connection between the first part of the telescopic dose drum and the inner circumferential surface of the housing has a pitch different to the pitch of the threaded connection of the inner circumferential surface of the second part of the telescopic dose drum and the threaded outer circumferential surface of the piston plunger.

In more detail, the distal part may comprise a helically or spirally extending groove on its outer side surface. The groove may extend all the way from the proximal end to the distal end of the distal part of the dose drum. The groove is intended to cooperate with at least one protrusion or spirally extending ledge segment arranged on the inner surface of the housing such that the dose drum is rotationally connected to the housing, whereby mutual rotation causes movement in the longitudinal direction of the parts. The distal end area of the first part of the dose drum is further arranged with a locking structure that engages with the locking structure of the drive drum sleeve when the drive drum sleeve is moved into the piston plunger during assembly of the medicament delivery device.

The inner circumferential surface of the second part of the telescopic dose drum may be threadedly connected to the threaded outer circumferential surface of the piston plunger. In particular, the proximal end of the second part may comprise a threaded structure. The threaded connection between the first part of the telescopic dose drum and the inner circumferential surface of the housing has a pitch different to the pitch of the threaded connection of the inner circumferential surface of the second part of the telescopic dose drum and the threaded outer circumferential surface of the piston plunger.

The piston plunger may comprises on its outer surface a stop feature for inhibiting rotation of the telescopic dose drum and the drive drum sleeve when the set dose equals the remaining dose in the medicament container.

The drive drum sleeve may be of generally tubular shape and is arranged radially inside the piston plunger. The drive drum sleeve may be provided with a distal end wall transversal to the longitudinal axis of the drive drum sleeve. The distal end wall has central opening and the drive drum sleeve is hollow in order to receive the resilient spinning element therein. The proximal end of the drive drum sleeve may comprise one or more, for example two, flexible arms extending in the proximal direction. The arms are flexible in that their proximal ends are radial deflectable upon application of a radial force thereon. The outer surface of each flexible arm may comprise a radially projecting piston plunger engagement protrusion for selectively engaging with the longitudinal splines or ribs on the inner surface of the piston plunger. The shape of the protrusions may generally correspond to the shape of the circumferentially arranged ribs on the piston plunger. The inner surface of each flexible arm may comprise a radially engagement protrusion for selective engagement with the resilient spinning element located within the hollow drive drum sleeve.

The distal end wall may forms a coupling element by means of two proximally extending locking arms. The locking arms comprise at their respective pouter surface a locking structure for locking the drive drum sleeve to the inner surface of a dose drum.

The resilient spinning element may comprise a longitudinal rod and a distal push button. The push button intended to act as a contact surface for a finger of a user during drug delivery. As described above, the longitudinal rod of the resilient spinning element is accommodated within the hollow drive drum sleeve. At its proximal end, the longitudinal rod may comprise an engagement structure comprising a first circumferential ring-like protrusion having a diameter larger than the diameter of the longitudinal rod and a second circumferential ring-like protrusion having a diameter larger than the diameter of the longitudinal rod. The second protrusion is preferably located at the proximal end of the longitudinal rod, and the first protrusion is located distal from the second protrusion. The first protrusion and the second protrusion are axially spaced from each other such that a circumferential groove is formed there between. The size of the groove and the location on the longitudinal groove may be such that the radially inwardly directed protrusion on the flexible arms of the drive drum sleeve is initially received in the groove. In such initial stage, the flexible arms are not deflected radially outwards but are in a tension-free state.

The axial length of the resilient spinning element in comparison to the drive drum sleeve is preferably such that in the initial state of the medicament delivery device, i.e. with the engagement protrusion being received in the groove, the proximal surface of the push button is spaced from the distal surface of the coupling element by a gap. This gap is maintained when a dose is set by a user and the first part of the dose drum, the drive drum sleeve and the resilient spinning element are moved distally. However, as soon as the push button is pushed pin proximal direction, the push button first bridges the gap thereby moving the longitudinal rod in proximal direction relative to the drive drum sleeve. Due to such relative displacement, the distally located first ring-shaped protrusion is pressed against the engagement protrusion on the flexible arms, thus deflecting the arms outwardly and into engagement with the longitudinal splines on the inner surface of the piston plunger.

The medicament delivery device may be an injection device, preferably a pen injector.

Other aspects, features, and advantages will be apparent from the summary above, as well as from the description that follows, including the figures and the claims.

BRIEF DESCRIPTION OF THE DRAWINGS

The figures below disclose an embodiment of the invention for illustrational purposes only. In particular, the disclosure within the figures is not meant to limit the range of protection of the invention. The embodiment shown may be modified in many ways within the scope of the claims.

DETAILED DESCRIPTION

Mechanical Structure of an Embodiment

Figure 1:
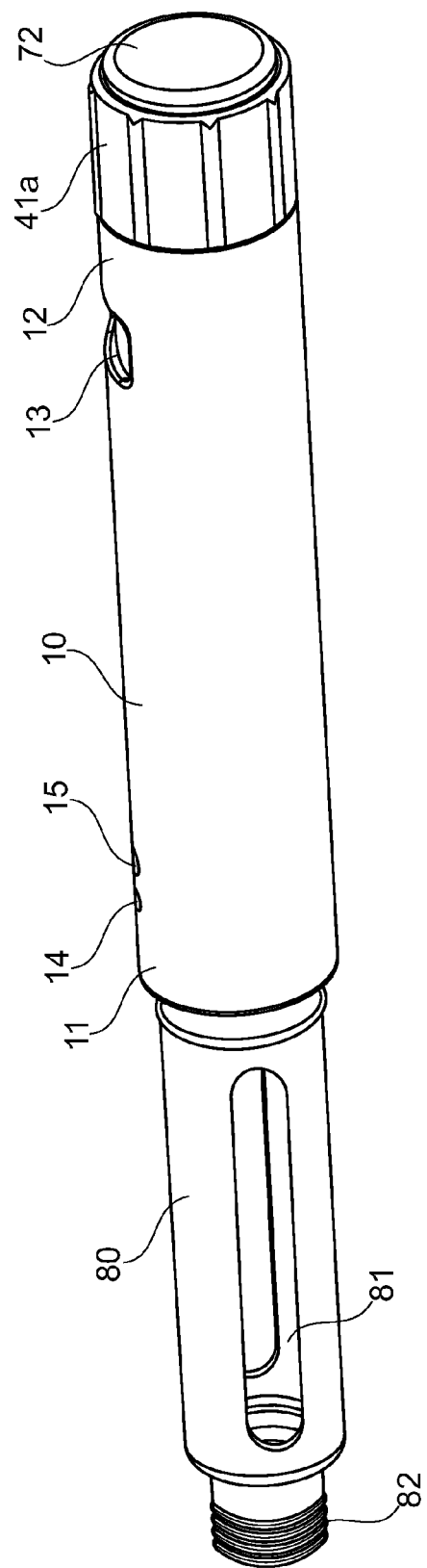
FIG. 1 shows a perspective view of a medicament delivery device according to a preferred embodiment of the invention, shown in the initial state.

FIG. 1 shows a perspective view of a medicament delivery device according to a preferred embodiment of the invention. The medicament delivery device has a proximal end and a distal end and comprises a housing 10 having a proximal part or end 11 and a distal part or end 12. In the assembled state of the medicament delivery device, the housing 10 forms part of the outer surface or appearance of the medicament delivery device. It is however to be understood that the housing may be designed in many other ways.

The medicament delivery device further comprises a medicament container holder 80 which accommodates a medicament container. The medicament container holder 80 also forms part of the outer surface or appearance of the medicament delivery device. The proximal part of the container holder 80 is further arranged with a neck 82 at its proximal end for attaching a per se known and conventional injection needle (not shown). It is however to be understood that other types of connection members, such as bayonet fitting luer-lock fittings and the like may be arranged. Also, the medicament container may have an injection needle integrated in its body whereby the neck portion 82 may be omitted.

A cap (not shown) may be provided for releasably covering the proximal end of the device, and thereby the proximal end of the medicament container holder 80, when not in use.

The medicament container holder 80 of the medicament delivery device comprises a window 81 that allows the user to view the progress of medicament delivery, i.e. whether the medicament delivery device is still in its initial stage with the medicament not yet being injected, or whether the medicament container is already emptied. Through window 81, the user can see the medicament container accommodated at least in the medicament container holder 80 (the distal part of the medicament container may reach into the proximal part of the housing 10). In a preferred embodiment, two such windows are provided located at opposite sides of the medicament container holder 80.

Furthermore, at the distal end 12 of the housing 10, a further window 13 is provided that is used to indicate a set dose to a user, as described in more detail below. At the distal end 12 of housing 10, a dose setting knob 41a for dose setting projects distally.

Figure 2:
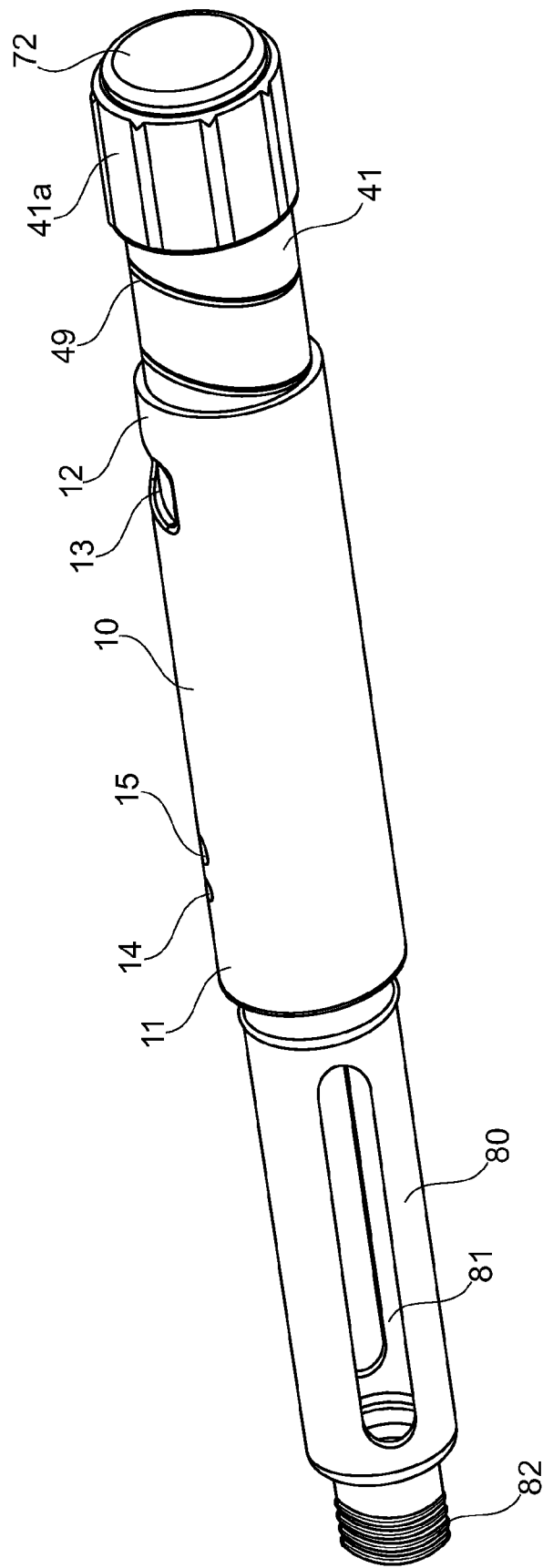
FIG. 2 shows a perspective view of a medicament delivery device according to the preferred embodiment of FIG. 1, shown in the state when a dose is set.

FIG. 1 shows the medicament delivery device in the initial state. When the user grasps the dose setting knob 41a and rotates it in a first direction, for example in clockwise direction, the dose setting knob 41a and other components move distally, as will be explained in detail below, in order to set a dose. FIG. 2 shows a perspective view of the medicament delivery device in such state, i.e. when a dose is set.

Figure 3:
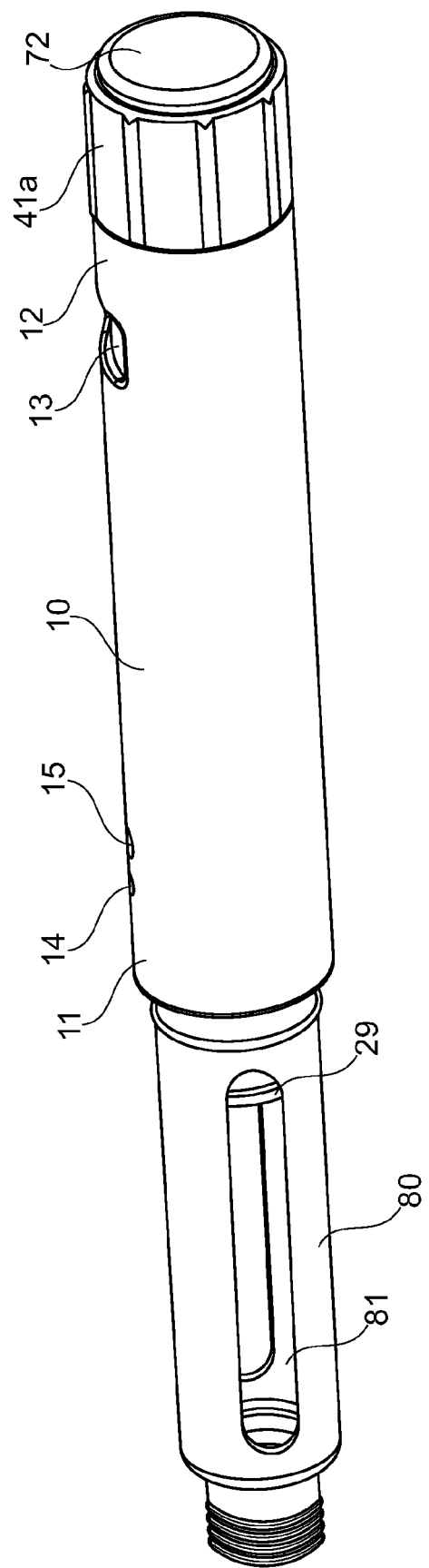
FIG. 3 shows a perspective view of a medicament delivery device according to the preferred embodiment of FIG. 1, shown after a set dose has been delivered.

FIG. 3 shows a perspective view of the medicament delivery device after a set dose has been delivered. As can be seen, the dose setting knob 41a and the components linked therewith were moved proximally and the dose setting knob 41a is again in its initial position. However, as can be seen at window 81, the piston plunger 20 of the medicament delivery device has been displaced in proximal direction and a stopper 29 within the medicament container can now be seen through the window(s) 81.

Figure 4:
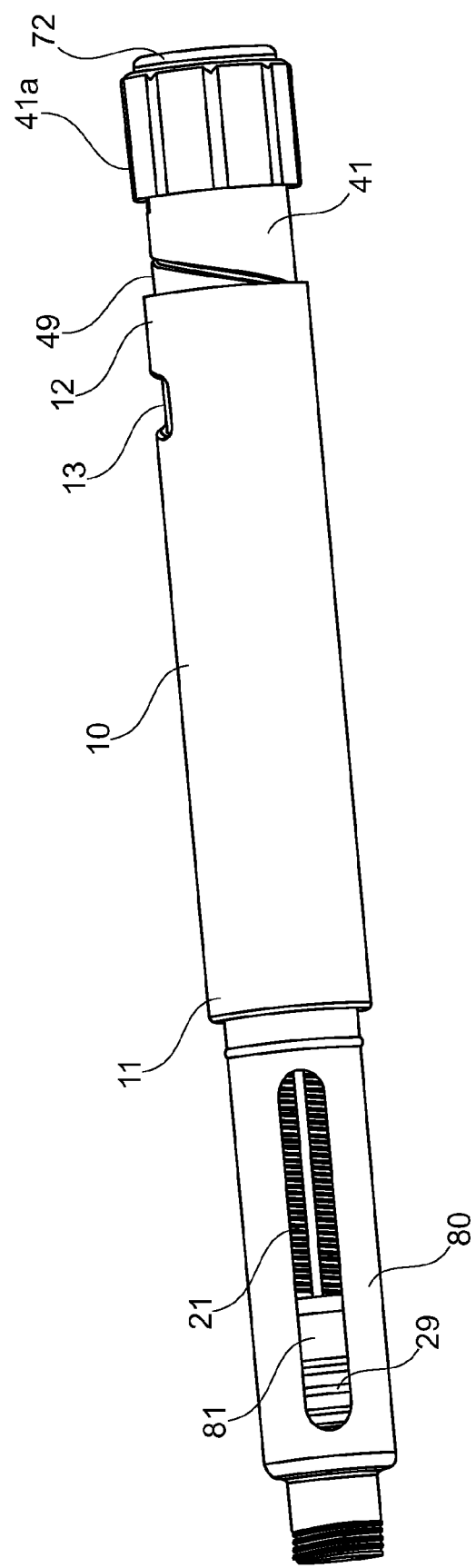
FIG. 4 shows a perspective view of a medicament delivery device according to the preferred embodiment of FIG. 1, shown in a state having all medicament delivered.

FIG. 4 then shows a perspective view of the medicament delivery device in a state having all medicament, i.e. several individual doses delivered. The stopper 29 is now located at the proximal end of the medicament container 85, and part of the piston plunger 20 with its threaded surface 21 can be seen through windows 81.

The medicament container holder 80 is arranged with attachment means for connecting or attaching it to the proximal housing part 11. In the embodiment shown the attachment means comprise a protrusion 83 (see FIG. 5) fitting into a corresponding recess 14. It is however to be understood that other attachment members may be utilized, such as bayonet fittings, threads, or the like for attaching the medicament container holder 80 with the housing 10.

An elongated piston plunger 20 (see FIGS. 5 to 7) is arranged inside the housing 10 and has a longitudinal axis generally corresponding with the longitudinal direction of the medicament delivery device. The piston plunger 20 is arranged with threads 21 on at least part of its outer surface. In the preferred embodiment shown in the drawings, a proximal part of the piston plunger 20 comprises a threaded structure 21. On its outer surface, the piston plunger 20 comprises at least one longitudinal groove 25 (in the shown embodiment, two such grooves 25 are provided). The proximal end of the piston plunger 20 is arranged with a washer or spinner 28 adapted to abut the stopper 29. The stopper 29 is intended to be movably received inside the medicament container 85.

Figure 5:
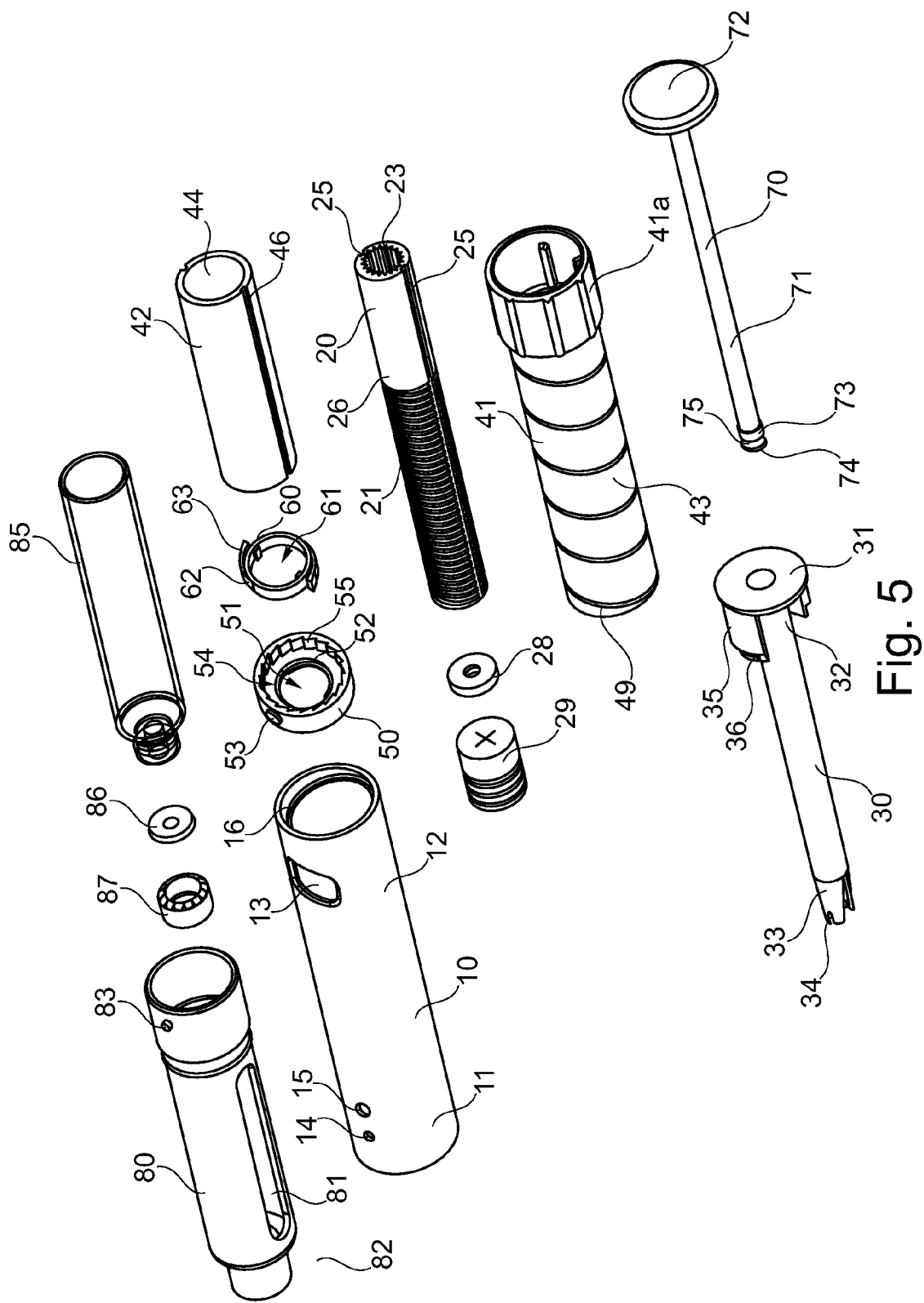
FIG. 5 shows an exploded view of the medicament delivery device according to the preferred embodiment of FIG. 1.

The piston plunger 20 fits into an insert 50 arranged with a central passage 51, the centre of which generally coincides with the longitudinal axis of the medicament delivery device. The central passage 51 of the thread insert is arranged with threads 52 of complementary design as the threads 21 of the piston plunger 20. The outer surface of the insert 50 comprises at least one protrusion 53 or the like, fitting into corresponding recesses 15 on the inner surface of the housing 10, whereby the insert 50 is locked to the proximal housing part 10. As shown in FIG. 5, recess 15 in the housing may be formed as a through hole.

The insert 50 further comprises a central bore 54 at the distal side of the thread insert 50. The diameter of the central bore 54 is larger than the diameter of the central passage 51 so that a stepped configuration is provided. The inner circumferential surface of the central bore 54 is arranged with a circumferentially extending ratchet 55 arranged with sawtooth shaped teeth.

Figure 7:
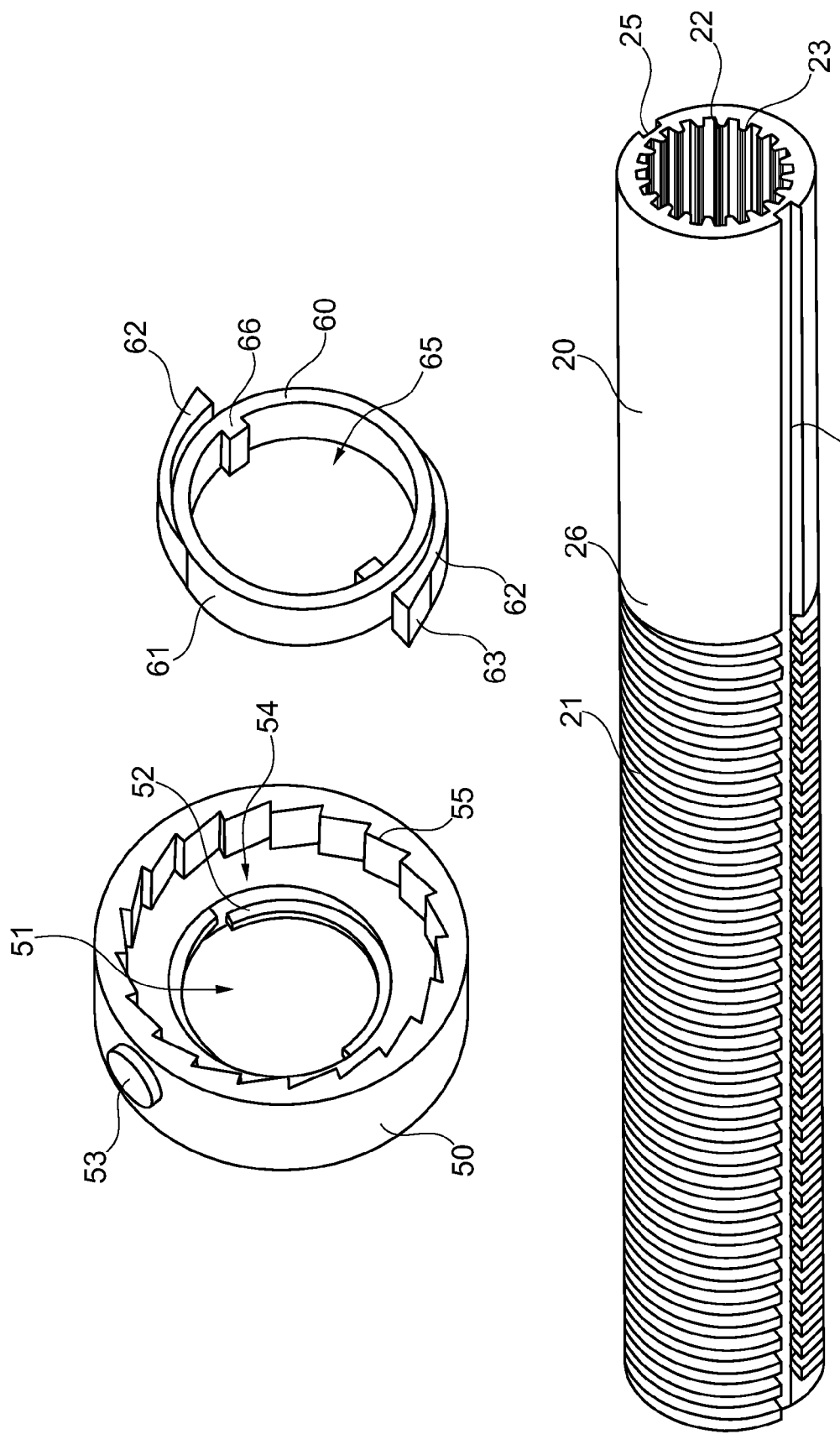
FIG. 7 shows another partly exploded view of the medicament delivery device according to FIG. 1.

The ratchet 55 cooperates with a ring-shaped back rotating blocking element 60 which is arranged with two oppositely positioned arms 62, extending on the outer circumferential surface 61 generally in the circumferential direction of the blocking element 60. Although two such arms 62 are shown in FIGS. 5 and 7, a single arm may as well suffice, or more than two arms may be provided, depending on the size of the blocking member 60. The one or more arms 62 are flexible in the generally radial direction. On the outwardly directed surfaces of the arm(s) 62, a ledge 63 is arranged. Each ledge 63 has a shape complementary to the ratchet 55 of the thread insert 50. The back rotating blocking element 60 is further arranged with a central passage 65 through which the piston plunger 20 extends. The central passage 65 is arranged with radially inwardly directed protrusions or ribs 66, which protrusions 66 fit into the elongated grooves 25 on the outer surface of the piston plunger 20. This structure provides a rotational lock of the piston plunger 20 but allows a movement of the piston plunger 20 in the longitudinal direction.

The piston plunger 20 is further arranged with a plurality of longitudinal splines or ribs 23 provided on the inner circumferential surface 22 of the hollow piston plunger 20. A drive drum sleeve 30 of generally tubular shape is arranged radially inside the piston plunger 20. The drive drum sleeve 30 is provided with a distal end wall 31 transverse to the longitudinal axis of the drive drum sleeve 30. The distal end wall 31 has a central opening and the drive drum sleeve is hollow in order to receive a resilient spinning element 70 therein, as will be described below. The proximal end of the drive drum sleeve 30 comprises one or more, preferably two, flexible arms 33 extending in the proximal direction. The arms 33 are flexible in that their proximal ends are radially deflectable upon application of a radial force thereon, as will be describe below. The outer surface of each flexible arm 33 comprises a radially projecting piston plunger engagement protrusion 34 for selectively engaging with the longitudinal splines 23 on the inner surface 22 of the piston plunger 25. The shape of the protrusions 34 generally corresponds to the shape of the circumferentially arranged ribs 23 on the piston plunger 20. The inner surface of each flexible arm 33 comprises a radial engagement protrusion 37 for selective engagement with the resilient spinning element 70 located within the hollow drive drum sleeve 30.

The distal end wall 31 forms a coupling element by means of two proximally extending locking arms 35. The locking arms 35 comprise at their respective outer surface a locking structure 36 for locking the drive drum sleeve 30 to the inner surface of a dose drum 40.

Outside the piston plunger 20 as seen in a radial direction, a telescopic dose (setting) drum 40 is arranged. The dose drum 40 has a generally tubular shape and is positioned coaxial with the piston plunger 20 as well as the housing 10. The dose drum 40 comprises a first, distal, part 41 and a second, proximal, part 42 being slidably arranged relative to each other. The distal part 41 is located coaxially radially outside of the proximal part 42 of the dose drum 40.

The distal part 41 comprises a helically or spirally extending groove 49 on its outer side surface 41. The groove 49 extends all the way from the proximal end to the distal end of the distal part 41 of the dose drum 40. The groove 49 is intended to cooperate with at least one protrusion or spirally extending ledge segment 16 (FIG. 5) arranged on the inner surface of the housing 10 such that the dose drum 40 is rotationally connected to the housing 10, whereby mutual rotation causes movement in the longitudinal direction of the parts. The distal end area of the first part 41 of the dose drum 40 is further arranged with a locking structure that engages with the locking structure 36 of the drive drum sleeve 30 when the drive drum sleeve 30 is moved into the piston plunger 20 during assembly of the medicament delivery device.

At the distal end of the first part 41 the dose setting knob 41a is arranged. The dose setting knob 41a comprises a proximally directed generally tubular part having a diameter somewhat larger than the outer surface of the first part 41 of the dose drum 40. The outermost diameter of the dose setting knob 41a is preferably flush with the outer diameter of housing 10. The first part 41 of the telescopic dose drum 40 is thus configured to rotationally move distally in the first direction relative to the housing 10 during dose setting by the dose setting knob 41a.

Figure 6:
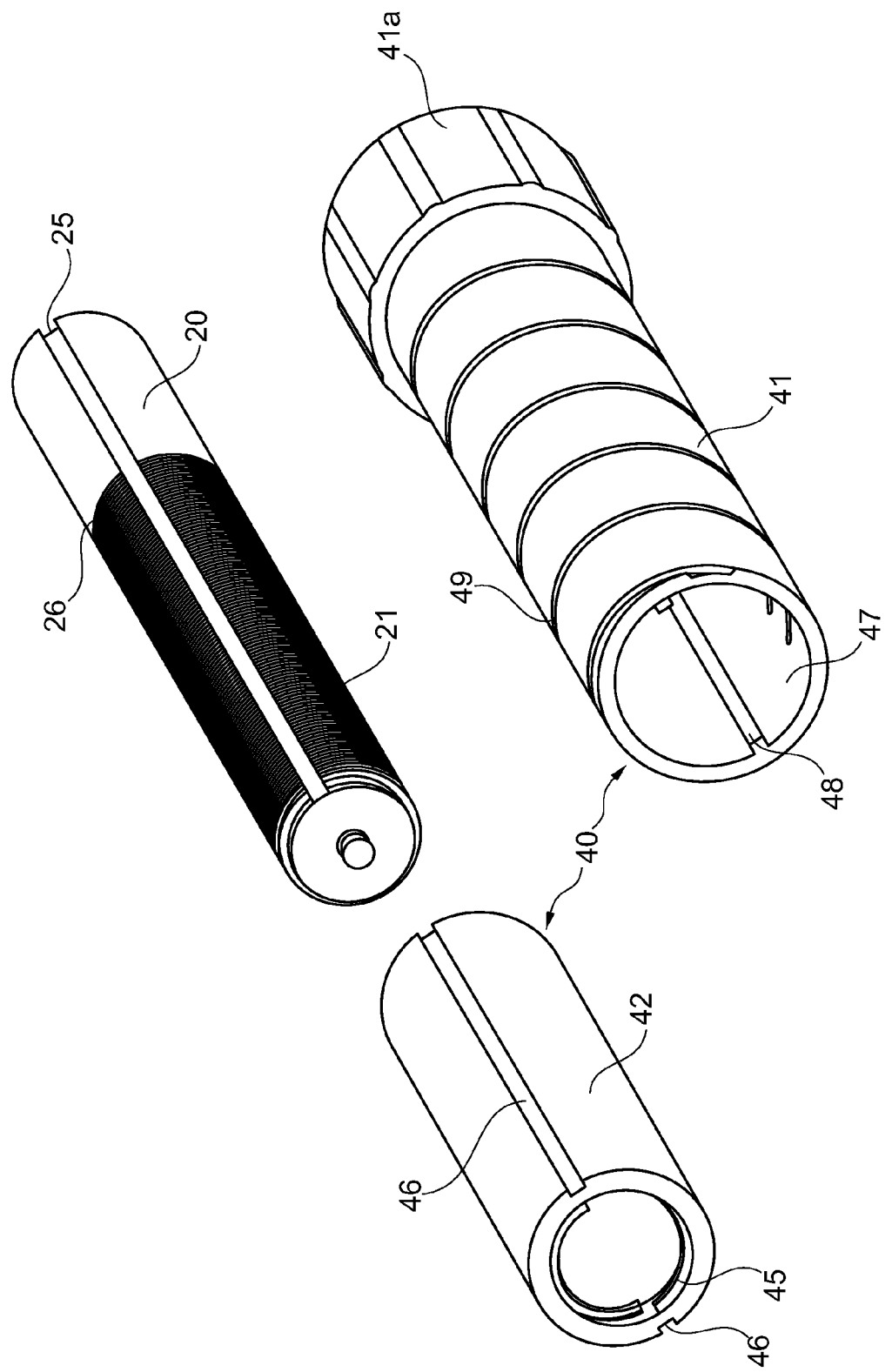
FIG. 6 shows a partly exploded view of the medicament delivery device according to FIG. 1.

The inner circumferential surface 44 of the second part 42 of the telescopic dose drum 40 is threadedly connected to the threaded outer circumferential surface 21 of the piston plunger 20. In particular, the proximal end of the second part 42 comprises a threaded structure 45 (FIG. 6). The threaded connection between the first part 41 of the telescopic dose drum 40 and the inner circumferential surface of the housing 10 has a pitch different to the pitch of the threaded connection of the inner circumferential surface 44 of the second part 42 of the telescopic dose drum 40 and the threaded outer circumferential surface 21 of the piston plunger 20.

As can also be seen in FIG. 6, the piston plunger 20 comprises on its outer surface a stop feature 26 for inhibiting rotation of the telescopic dose drum 40 and the drive drum sleeve 30 when the set dose equals the remaining dose in the medicament container.

The resilient spinning element 70 comprises a longitudinal rod 71 and a distal push button 72. The push button intended to act as a contact surface for a finger of a user during drug delivery, as will be described. As described above, the longitudinal rod 71 of the resilient spinning element 70 is accommodated within the hollow drive drum sleeve 30. At its proximal end, the longitudinal rod 71 comprises an engagement structure comprising a first circumferential ring-like protrusion 73 having a diameter larger than the diameter of the longitudinal rod and a second circumferential ring-like protrusion 74 having a diameter larger than the diameter of the longitudinal rod. The second protrusion 74 is preferably located at the proximal end of the longitudinal rod, and the first protrusion 73 is located distal from the second protrusion 74. The first protrusion 73 and the second protrusion 74 are axially spaced from each other such that a circumferential groove 75 is formed there between. The size of the groove 75 and the location on the longitudinal rod 71 is such that the radially inwardly directed protrusion 37 on the flexible arms 33 of the drive drum sleeve 30 is initially received in the groove 75. In such initial stage, the flexible arms 33 are not deflected radially outwards but are in a tension-free state.

Figure 8:
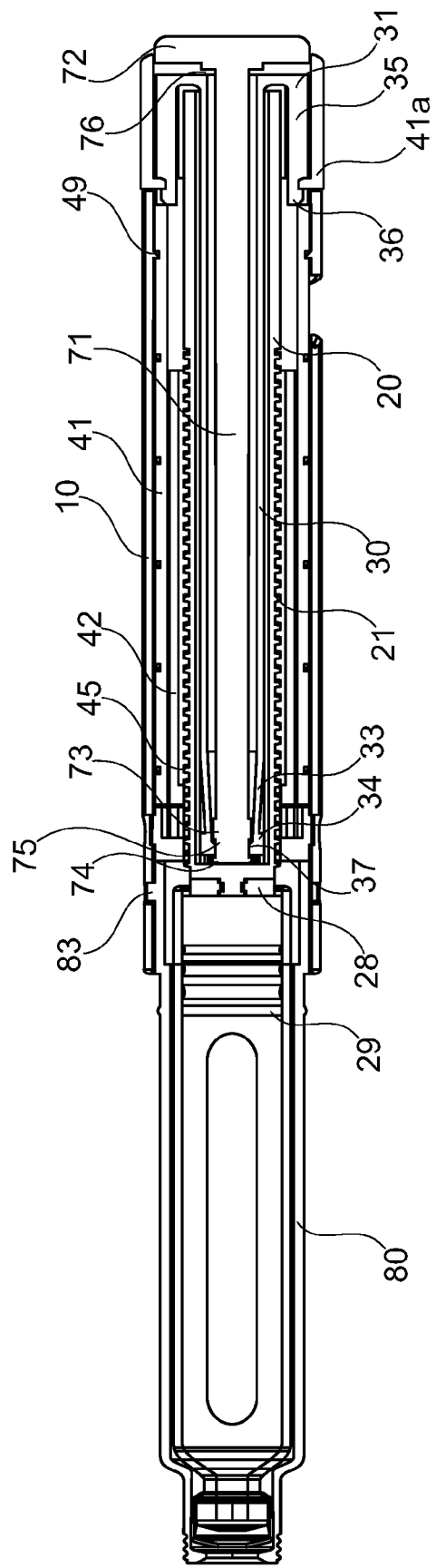
FIG. 8 shows a cross-sectional view of the medicament delivery device according to FIG. 1, shown in the initial state.

The axial length of the resilient spinning element 70 in comparison to the drive drum sleeve 30 is such that in the initial state of the medicament delivery device, i.e. with the engagement protrusion 37 being received in the groove 75, the proximal surface of the push button 72 is spaced from the distal surface of the coupling element 31 by a gap 76 (see, e.g., FIG. 8). This gap 76 is maintained when a dose is set by a user (see FIG. 9) and the first part 41 of the dose drum 40, the drive drum sleeve 30 and the resilient spinning element 70 are moved distally. However, as soon as the push button 72 is pushed towards the proximal direction, the push button 72 first bridges the gap 76 thereby moving the longitudinal rod 71 in proximal direction relative to the drive drum sleeve 30. Due to such relative displacement, the distally located first ring-shaped protrusion 73 is pressed against the engagement protrusion 37 on the flexible arms 33, thus deflecting the arms 33 outwardly and into engagement with the longitudinal splines on the inner surface 22 of the piston plunger 20. Moreover, as soon as the push button 72 is released, the deflected arms 33 strive to move inwardly such that the engagement protrusion 37 are received in the groove 75 whereby the longitudinal rod 71 is moved in the distal direction relative to the drive drum sleeve 30. It is also possible that the device further comprises a resilient member arranged in the gap 76, wherein said resilient member is a sole component or is integral with either the drive drum sleeve 30 or the resilient spinning element 70.

Description of the Function and Operation of the Embodiment

Setting Operation for a Dose to be Delivered

FIG. 8 shows a cross-sectional view of the medicament delivery device in the initial state.

In order for a dose to be delivered, the device must be operated to set a dose. In order to set a dose to be delivered the user grips the housing 10 and the distally arranged dose setting knob 41a and turns them in relation to each other, where the dose setting knob 41a is turned in the clockwise direction, for example. The turning of the dose setting knob 41a will cause the first part 41 of the dose drum 40 to be rotated. The connection between the helical groove 49 of the dose drum 40 and the spiral ledge segment of the housing 10, the rotation will cause the first part 41 of the dose drum 40 to move in the distal direction in relation to the housing 10. Inside the dose setting drum 40 the drive drum sleeve 30 will also rotate because of the rotational lock both at the distal end 31 of the drive drum sleeve 30 with the dose drum 40. Thus the drive drum sleeve 30 is rotationally connected to the dose drum 40.

The longitudinal ribs 48 on the inner surface of the first part 41 of the dose drum 40 are in contact with the longitudinal grooves on the outer surface of the second part 42 of the dose drum 40. Thus, the first part can slide relative to the second part. Furthermore, the second part 42 is also rotated and due to the threaded 45 engaging into the threaded surface of the piston plunger 20, the second part 42 also moves distally, albeit at a lower speed than the first part 41 due to the different pitches. Rotation of the second part 42 also causes a certain turning force on the piston plunger 20, which also urges the back rotating blocking element 60 to turn due to the rotational lock between the blocking element 60 and the piston plunger 20 because of the protrusions 66 of the back rotating blocking element 60 fitting into the longitudinal grooves 25 of the piston plunger 20. However, the arms 62 of the back rotating blocking element 60 are directed such and cooperating such with the ratchet 55 of the thread insert 50 that any rotation of the back rotating blocking element 60 is prevented. Thus the piston plunger 20 is prevented from rotating. During rotation, preferably indicia (not shown) on the dose drum 40 are shown through the window or opening 13 at the distal end 12 of the housing 10. The patient thus rotates the dose setting knob 41a until the prescribed dose quantity is displayed.

If the user by mistake has set a too large dose, he/she simply turns the dose setting knob 41a in the opposite direction, whereby both the dose drum 40 and the drive drum sleeve 30 are turned in the opposite direction until the correct dose has been reached.

Figure 9:
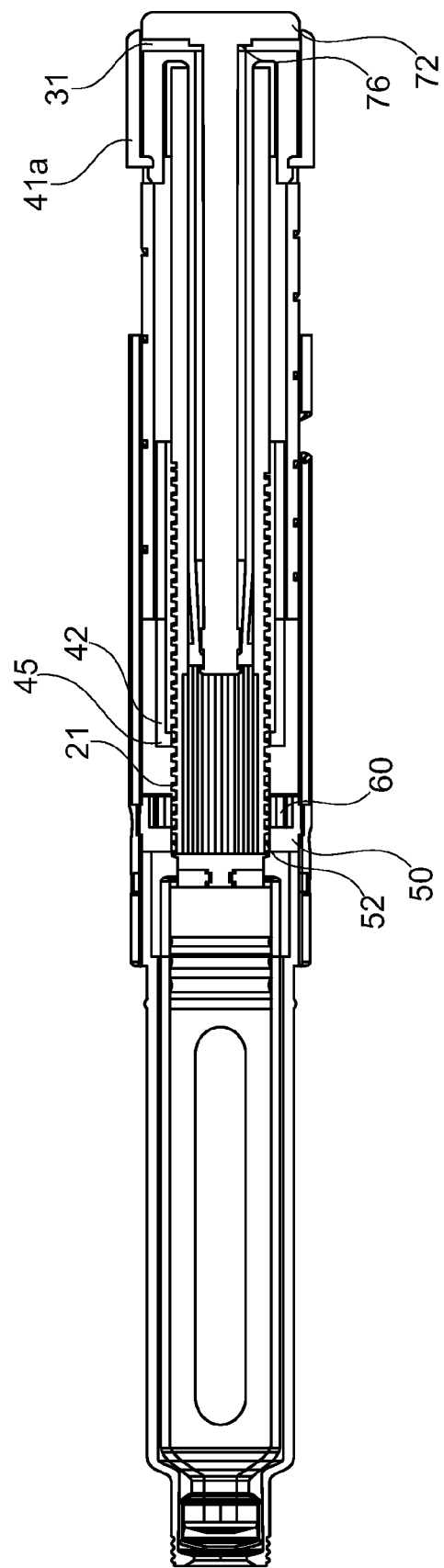
FIG. 9 shows a cross-sectional view of the medicament delivery device according to FIG. 2, i.e., in the state when a dose is set.

FIG. 9 shows a cross-sectional view of the medicament delivery device in the state when a dose is set. In particular, it can be seen that the gap 76 still exists.

Delivery Operation of a Pre-Set Dose of Medicament

In order to deliver a dose of medicament, the user presses the proximal end of the device against a dose delivery site, and in particular an injection site when the medicament delivery member is an injection needle. The next step is to press on the push button 72 at the distal end of the device.

Figure 10:
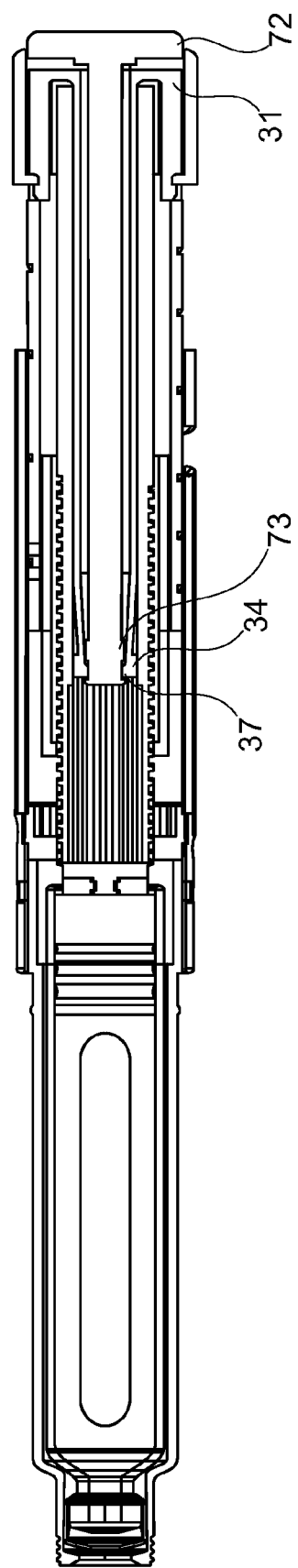
FIG. 10 shows a cross-sectional view of the medicament delivery device at the beginning of the process of dose delivery.

FIG. 10 shows a cross-sectional view of the medicament delivery device at the beginning of the process of dose delivery. As can be seen, the gap 76 is now closed due to the force applied by the user and the button 72 contacts the distal coupling member 31 of the drive drum sleeve 30.

The force on the push button 72 will first bring the drive drum sleeve 30 into engagement with the inner surface of the piston plunger 20, as already described above. Secondly, once the gap 76 has been bridged, the force on the push button 72 urges the dose activator knob 41a in the proximal direction. This proximal force will be transferred to the dose drum 40 and due to the threaded connection with the housing 10, the dose setting drum 40 will rotate, now in the anti-clockwise direction, and move in the proximal direction. Because of the rotational lock between the dose drum 40 and the drive drum sleeve 30, the latter will also rotate. Due to the radial flexing of the arms 33 of the drive drum sleeve 30, the inwardly directed protrusions 34 of the drive drum sleeve 30 firmly engage the splines 23 of the piston plunger 20.

Thus when now the dose drum 40 and the drive drum sleeve 30 rotate, the latter will urge the piston plunger 20 to rotate as well. This rotation in the anti-clockwise direction will be allowed by the back rotating blocking element 60 due to the design of its arms 62 in contact with the ratchet 55 of the thread insert 50. The piston plunger 20 will thus rotate together with the back rotating blocking element 60, and the arms 62 of the back rotating blocking element 60 sliding over the ratchet 55 of the thread insert 50 will provide audible and tactile information. Further the rotation of the piston plunger 20 will cause it to be moved in the proximal direction due to the threaded connection with the thread insert 50, whereby the movement of the piston plunger 20 will urge the stopper 29 in the proximal direction, thereby expelling a dose of medicament through the dose delivery member. The dose has been delivered when the dose drum 40 has moved back to its initial position, which could be limited by some sort of blocking member (not shown) preventing further movement or rotation of the dose drum.

Figure 11:
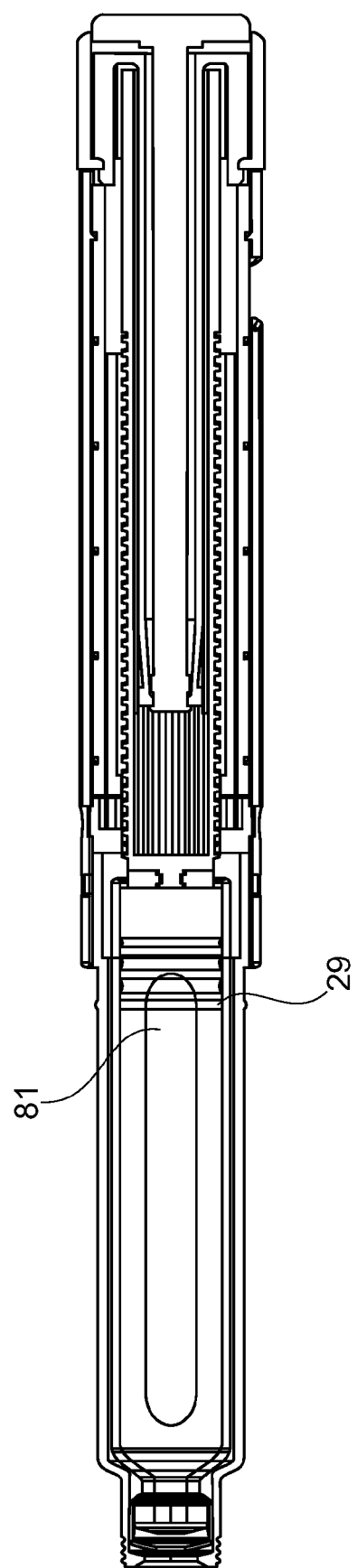
FIG. 11 shows a cross-sectional view of the medicament delivery device according to FIG. 3, i.e., after a set dose has been delivered.

FIG. 11 shows a cross-sectional view of the medicament delivery device after a set dose has been delivered.

The device may now be removed from the dose delivery site, and the medicament delivery member discarded. If the medicament container 85 still contains a large enough dose to be delivered, the above steps may be repeated from the step "Setting operation for a dose to be delivered".

Figure 12:
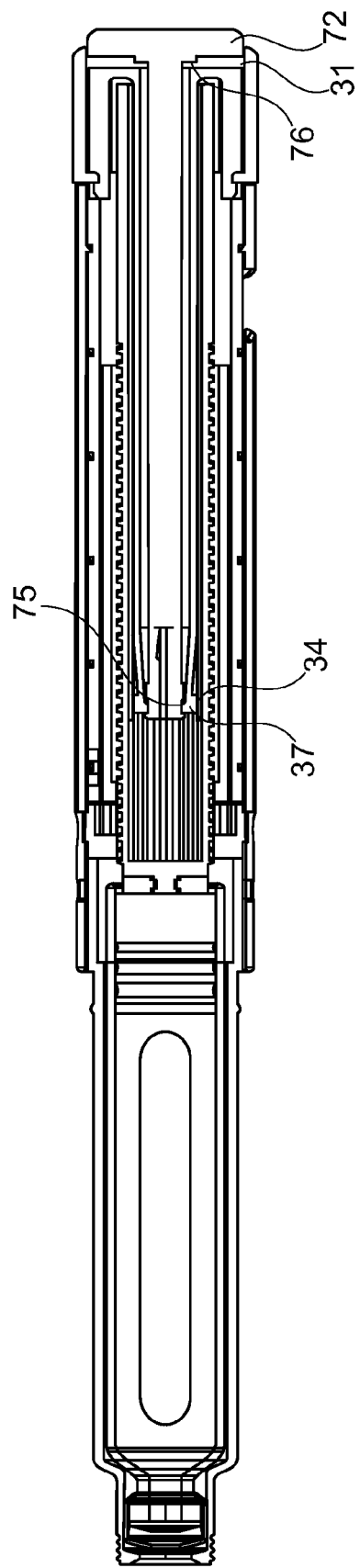
FIG. 12 shows a cross-sectional view of the medicament delivery device at the beginning of the process of setting a new dose.

FIG. 12 shows a cross-sectional view of the medicament delivery device at the beginning of the process of setting a new dose.

Figure 13:
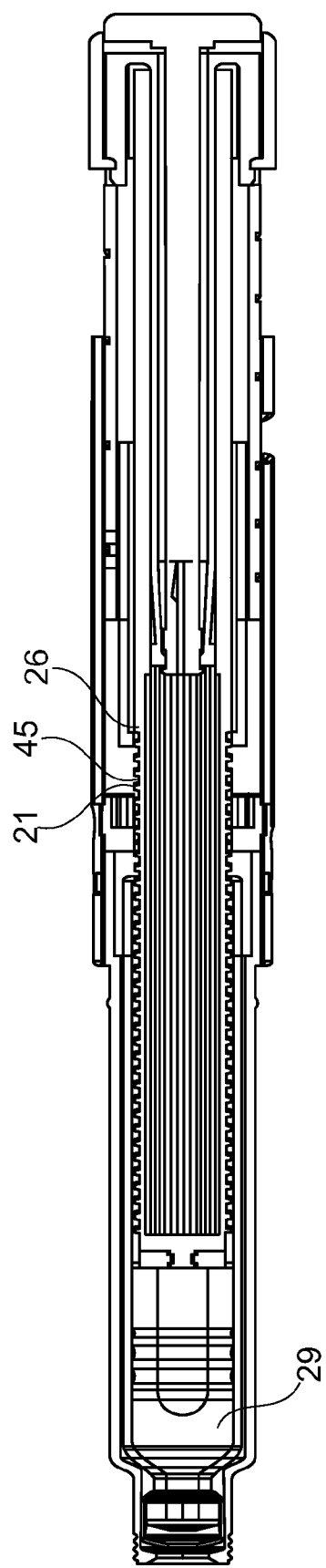
FIG. 13 shows a cross-sectional view of the medicament delivery device according to FIG. 4, i.e., in a state having all medicament delivered.

FIG. 13 shows a cross-sectional view of the medicament delivery device in a state having all medicament delivered. The stopper 29 is located at the proximal wall of the medicament container.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A medicament delivery device, comprising:
a housing having a proximal end and a distal end;
a hollow piston plunger being arranged within the housing;
a telescopic dose drum being concentrically arranged between the housing and the piston plunger, the telescopic dose drum being bidirectional movable in relation to the housing and in relation to the piston plunger when setting a dose and delivering a dose, wherein the telescopic dose drum comprises a first, distal part and a second, proximal part being slidably arranged relative to each other; and
piston plunger driving means for driving the hollow piston plunger towards the proximal end characterized in that the piston plunger driving means comprises
a hollow drive drum sleeve being movably arranged within the hollow piston plunger and being fixedly connected to the telescopic dose drum, wherein the hollow drive drum sleeve and the hollow piston plunger are releasably coupleable to each other; and a resilient spinning element having a longitudinal rod being movably arranged within the hollow drive drum sleeve, wherein the longitudinal rod and the hollow drive drum sleeve are releasably coupleable to each other;

such that after a dose is set, axial movement of the resilient spinning element towards the proximal end forces the longitudinal rod and the hollow drive drum sleeve to couple together and thereby the hollow drive drum sleeve and the hollow piston plunger also to couple together whereby the hollow piston plunger and the telescopic dose drum are displaced towards the proximal end for delivering the set dose, and such that after a set dose is delivered, axial movement of the resilient spinning element towards the distal end forces the longitudinal rod and the hollow drive drum sleeve to decouple and thereby the hollow drive drum sleeve and the hollow piston plunger also to decouple for setting a new dose.

2. The medicament delivery device of claim 1, wherein the resilient spinning element is configured to be axially spaced from a distal part of the hollow drive drum sleeve during setting a dose by a user, and to abut against the distal part of the hollow drive drum sleeve during delivery of a set dose.

3. The medicament delivery device of claim 1, further comprising a dose setting knob at a distal end of the first part of the dose drum, the dose setting knob configured to be grasped by a user for setting a dose when being rotated in a first direction.

4. The medicament delivery device of claim 3, wherein the dose setting knob is a separate component connected with the distal end of the first part of the dose drum, or wherein the dose setting knob is integral with the first part, whereby the first part of the telescopic dose drum is configured to rotationally move distally in a first direction relative to the housing during dose setting by the dose setting knob.

5. The medicament delivery device of claim 1, further comprising a medicament container holder adapted to receive a medicament container.

6. The medicament delivery device of claim 1, further comprising an unidirectional means for preventing movement of the piston plunger in a distal direction during setting a dose.

7. The medicament delivery device of claim 6, wherein part of an outer circumferential surface of the piston plunger is threaded.

8. The medicament delivery device of claim 7, wherein the unidirectional means comprises an insert having a central longitudinal passage having a first diameter, the passage being provided with threads mating with the threads of the outer circumferential surface of the piston plunger, wherein the insert, in an initial position of the medicament delivery device, is located at a proximal end of the piston plunger.

9. The medicament delivery device of claim 8, wherein a distal side of the insert further comprising a central bore coaxial with the central longitudinal passage, the central bore having a second diameter being larger than the first diameter, an inner surface of the bore being provided with a circumferentially extending ratchet.

10. The medicament delivery device of claim 9, wherein the unidirectional means further comprises a back rotation blocking element, comprising at its circumferential surface at least one arm extending in circumferential direction and being flexible in radial direction, the at least one arm comprising a ledge, the ledge having a shape complementary to the ratchet of the insert.

11. The medicament delivery device of claim 10, wherein the at least one arm with its ledge is resilient such that rotation of the back rotation blocking element against the ratchet during medicament delivery generates an audible feedback.

12. The medicament delivery device of claim 10, the back rotation blocking element comprising a longitudinal central passage having at least one radially inwardly directed protrusion, the at least one protrusion being each received in a corresponding longitudinal groove on the outer surface of the piston plunger.

13. The medicament delivery device of claim 10, wherein the ratchet comprises steep front edges and ramp shaped trailing edges such that the interaction of the ratchet with the at least one arm is to have a unidirectional coupling for the piston plunger.

14. The medicament delivery device of claim 8, wherein the insert is a separate component being fixedly connected to the housing or wherein the insert is a component integral with the housing.

15. The medicament delivery device of claim 8, wherein the unidirectional means comprises a self-locking thread connection between a threaded mating between the insert and the piston plunger.

16. The medicament delivery device of claim 7, wherein the unidirectional means comprises an insert having a central longitudinal passage having a first diameter, the central longitudinal passage having at least one radially inwardly directed protrusion, the at least one protrusion being each received in a corresponding longitudinal groove on the outer surface of the piston plunger.

17. The medicament delivery device of claim 16, a distal side of the insert further comprising a central bore coaxial with the central longitudinal passage, the central bore having a second diameter being larger than the first diameter, an inner surface of the bore being provided with a circumferentially extending ratchet.

18. The medicament delivery device of claim 17, wherein the unidirectional means further comprises a back rotation blocking element having a central longitudinal passage having a first diameter, the passage being provided with threads mating with the threads of the outer circumferential surface of the piston plunger, wherein the back rotation blocking element, in an initial position of the medicament delivery device, is located at a proximal end of the piston plunger.

19. The medicament delivery device of claim 18, wherein the back rotation blocking element comprises at its circumferential surface at least one arm extending in circumferential direction and being flexible in radial direction, the at least one arm comprising a ledge, the ledge having a shape complementary to the ratchet of the insert.

20. The medicament delivery device of claim 1, wherein an inner circumferential surface of the piston plunger comprises a plurality of longitudinally extending splines and the drive drum sleeve comprises at least one flexible arm being configured to releasably engage with the plurality of longitudinally extending splines of the piston plunger.

21. The medicament delivery device of claim 20, wherein the longitudinal rod of the resilient spinning element is operably connected with the hollow drive drum sleeve such that an axial movement of the resilient spinning element in proximal direction forces the at least one flexible arm to engage with the plurality of longitudinally extending splines of the piston plunger.

22. The medicament delivery device of claim 21, wherein the longitudinal rod comprises an engagement structure comprising a first circumferential ring-like protrusion having a diameter larger than a diameter of the longitudinal rod and a second circumferential ring-like protrusion having a diameter larger than the diameter of the longitudinal rod, wherein the first protrusion and the second protrusion are axially spaced from each other such that a circumferential groove is formed there between such that a radially inwardly directed protrusion on the at least one flexible arm of the drive drum sleeve is initially received in the groove such that the at least one flexible arm is not deflected radially outwards but are in a tension-free state.

23. The medicament delivery device of claim 1, wherein the resilient spinning element is configured to stay rotationally immobilized during axial movement thereof.

24. The medicament delivery device of claim 1, wherein an outer circumferential surface of the first part of the telescopic dose drum is threadedly connected to a mating structure on an inner circumferential surface of the housing.

25. The medicament delivery device of claim 1, wherein an inner circumferential surface of the second part of the telescopic dose drum is threadedly connected to a threaded outer circumferential surface of the piston plunger.

26. The medicament delivery device of claim 25, wherein the threaded connection between the first part of the telescopic dose drum and an inner circumferential surface of the housing has a pitch different to a pitch of the threaded connection of the inner circumferential surface of the second part of the telescopic dose drum and the threaded outer circumferential surface of the piston plunger.

27. The medicament delivery device of claim 1, wherein an outer surface of the piston plunger comprises a stop feature for inhibiting rotation of the telescopic dose drum and the drive drum sleeve when the set dose equals the remaining dose in a medicament container.

28. The medicament delivery device of claim 1, wherein the device is an injection device, preferably a pen injector.

* * * * *